United States Patent [19]
Slezak et al.

[11] Patent Number: 5,375,606
[45] Date of Patent: Dec. 27, 1994

[54] BIO-ANALYTICAL SEPARATION METHOD

[75] Inventors: Sue E. Slezak, Downingtown; Brian D. Gray, Ardmore; Gregory A. Kopia, Phoenixville, all of Pa.

[73] Assignee: Zynaxis, Inc., Malvern, Pa.

[21] Appl. No.: 486,618

[22] Filed: Feb. 28, 1990

[51] Int. Cl.$^5$ .............................. A61B 5/0275
[52] U.S. Cl. .................... 128/691; 128/898; 424/9
[58] Field of Search ............ 128/653.3, 691, 692, 128/898; 424/4, 9

[56] References Cited

U.S. PATENT DOCUMENTS

| | | |
|---|---|---|
| 4,372,745 | 2/1983 | Mandle et al. |
| 4,576,912 | 3/1986 | Yaverbaum et al. |
| 4,616,658 | 10/1986 | Shell et al. .......... 128/691 |
| 4,698,263 | 10/1987 | Wagner et al. |
| 4,717,676 | 1/1988 | Wagner et al. |
| 4,748,129 | 5/1988 | Chang et al. |
| 4,783,401 | 10/1988 | Horan et al. |
| 4,811,741 | 3/1989 | Shell et al. .......... 128/691 |
| 4,912,208 | 3/1990 | Fiechtner et al. ..... 536/53 |

FOREIGN PATENT DOCUMENTS

| | | | |
|---|---|---|---|
| 461503 | 12/1991 | European Pat. Off. | 128/691 |
| 2210406 | 9/1973 | Germany | 128/691 |

OTHER PUBLICATIONS

H. Alfthan & U. Stenman, Am. Biotech Lab 6: 8-13 (1987).
V. Ghazarrozian et al., Clin. Chem. 34: 1720-25 (1988).
D. Lewinsohn et al., Immunol. Meth. 110: 93-100 (1988).
P. Machy et al., Proc. Natl. Acad. Sci. USA 79: 4148-52 (1982).
D. Monroe, Amer. Biotech Lab 6: 10-19 (1987).
J. Sunamoto et al., Biochim. Biophys. Acta 898: 323-30 (1987).
A. Truneh et al., J. Immunol. Methods 100: 59-71 (1987).

Primary Examiner—Angela D. Sykes
Attorney, Agent, or Firm—Dann, Dorfman, Herrell and Skillman

[57] ABSTRACT

A separation method for use in conjunction with bio-analytical techniques, such as cell screening and blood flow measurement, in which a carrier bearing a bio-affecting compound comprising a reporter moiety is contacted with an organic extractant which is immiscible with the carrier, so as to produce distinct extractant and carrier phases, with a major amount of the bio-affecting compound originally associated with the carrier being transferred to the extractant phase. The separation method is particularly useful in performing bio-analytical techniques involving fluorometric determinations, as fluorescence efficiency is increased substantially by transfer of a fluorescent reporter from an aqueous carrier phase to the organic extractant phase, and concentration of the fluorescent reporter in the extractant phase prior to fluorescence measurement.

7 Claims, 1 Drawing Sheet

BIO-ANALYTICAL SEPARATION METHOD

FIELD OF THE INVENTION

The present invention relates to biological testing procedures and in particular to an improvement in cell screening and other bio-analytical techniques in which an analyte or reagent is provided with a detectable reporter to measure a specific property or condition of the analyte, or of the test system in which the reagent is used.

DESCRIPTION OF THE PRIOR ART

The use of analytes and test reagents coupled to detectable reporters, such as radioisotopes, dyes, enzymes and the like, is quite common in many current bio-analytical techniques. In flow cytometry, for example, a fluorochrome may be selectively bound via coupling through a monoclonal antibody or other specific binding substance to a characteristic determinant of a cell or cell constituent of interest, such as a surface antigen or receptor, and the fluorescence of the fluorochrome is thereafter measured. Flow cytometry is commonly used for cell screening, as it provides invaluable information regarding cell number or frequency and antigen density which greatly facilitates clinical diagnosis and therapeutic decision-making, especially in the fields of immunology, hematology and oncology.

While flow cytometry possesses certain notable advantages over other commonly used cell marker analysis techniques, such as immunofluorescence microscopy, immunocytochemistry and enzyme immunoassay, particularly with respect to speed, accuracy of results and heightened sensitivity for detection of weakly fluorescent cells, it is not without certain shortcomings. One distinct disadvantage of flow cytometry is that it must be performed on individual cells. Consequently, flow cytometry is not generally applicable to tissues. Rather, current clinical applications of flow cytometry are confined primarily to the study of immunological or neoplastic disorders of peripheral blood, bone marrow or other tissues that are relatively easily dissociated into single cell suspensions. Moreover, the capital investment and operating expense for the flow cytometer itself are substantial, given the sophisticated electronics and data analysis systems incorporated therein. This high cost restricts availability of flow cytometers to relatively large laboratories.

In flow cytometry, as well as in other bio-analytical techniques which involve labelling of an immunoreactive molecule directly with detectable reporters, the number of reporter molecules that may be bound to the immunoreactive molecule without changing its immunoreactivity is limited. Moreover, the covalent bonding of a reporter molecule to an immunoreactive molecule requires compatible reactive groups on each molecule, which imposes another practical limitation on this direct labelling technique.

In order to avoid direct labelling of fluorescent reporters to antibodies for use in flow cytometry and fluorescence microscopy, it has been proposed to use reagents comprising antibodies attached to liposomes loaded with dye molecules entrapped in the aqueous phase inside the liposomes. The increased number of reporter molecules per antibody has been found to enhance signal amplification. Furthermore, encapsulation of the reporter within the liposome is said to permit a wider range of reporter molecules to be used, including those that cannot be directly bound to antibody. See: A. Truneh et al., J. Immunol. Methods, 100:59–71 (1987) and references cited therein; and U.S. Pat. No. 4,372,745 to R. Mandle et al.

Similar reagents have been proposed for use in other diagnostic applications. The patent literature discloses immunoassays utilizing reagents in which a specific binding substance for an immunoreactive substance of interest is fixed on lipid membrane-containing microcapsules, having a hydrophilic marker encapsulated in the microcapsules. In performing such immunoassays, a test sample containing the immunoreactive substance of interest is mixed with the reagent and a source of complement causing the marker to be released from the microcapsules, after which its presence or quantity is determined by appropriate analysis. See for example, Japanese Patents 60159652-A and 60017359-A. According to the specific embodiments disclosed in these references, the microcapsules are liposomes which are fixed to the specific binding substance via covalent bonds. See also: Japanese Patents 60138464-A, 60138465-A and 60138466-A. One reported advantage of this method is the ability to measure bound reagent in the presence of unbound reagent. However, the method also has several notable disadvantages. First, complement is a labile reagent and false negatives may result in this method from failure of complement to properly lyse liposomes and release reporter. Second, if the disclosed reagent were used to determine cell surface associated structures, complement could cause lysis of cells as well as liposomes, releasing substances which may interfere with measurement of some reporter molecules. Third, microenvironments within some test samples (e.g., low pH) may cause significant leakage and nonspecific release of some reporter molecules (e.g., carboxyfluorescein; P. Machy et al., Proc. Nat. Acad. Sci. USA 79:4148 (1982)).

Liposome reagents have also been proposed for use in determining soluble analytes, as described, for example, in U.S. Pat. Nos. 4,717,676 and 4,698,263.

A tissue or cell specific drug-delivery reagent comprising a polysaccharide-coated liposome is described in Sunamoto et al., Biochem. Biophys. Acta, 898:323 (1987). The polysaccharide moiety (pullulan) is covalently conjugated to cholesterol and to antibody IgM fragment. One method described for determining attachment of the liposomes to the surface of target cells was incorporation of a hydrophobic fluorescent probe, terbium trisacetylacetonate, in the lipid membranes and examination of the stained cell surface by fluorescence microscopy.

Another way of overcoming the above-noted limitation of directly coupling fluorescent reporter molecules to antibodies in fluoroimmunoassays is described in U.S. Pat. No. 4,576,912 to S. Yaverbaum et al. The immunoassay technique disclosed therein involves the use of a reagent comprising a carrier bearing a plurality of closely-packed fluorophores, which is coupled to an immunological reactant competitive with the immunological reactant of interest. The fluorophores are sufficiently closely packed as to exhibit self-quenching and the reagent is capable of undergoing chemical treatment to release the fluorophores. A test sample and the reagent are mixed with a solid phase bearing a specific binding substance for the immunological reactant of interest, with which the reagent competes. After the competitive-binding reaction occurs, the bound immunological reactants and unbound immunological reactants are separated. The carrier, in either or both separated portions, is then chemically treated, or lysed, to liberate the otherwise quenched, closely-packed fluorophores to greatly enhance the measured fluorescence. The fluorescence intensity of the liberated fluorophores is then compared to a standard of known concentration to determine the amount of immunological reactant in the sample. This immunoassay technique is not without certain drawbacks, however, in that it utilizes covalent coupling of the reporter molecules to the carrier and a subsequent chemical reaction, which is typically a time consuming enzymatic reaction, to effect reporter release prior to detection.

Time-resolved immunofluorometric assays have been disclosed in which rare earth metals are used as reporters. See Alfthan et al., Am. Biotech. Lab., 6, (6), 8–13 (1988) and references cited therein. Such assays generally involve use of aminopolycarboxylic acid chelates of rare earth metals (in practice $Eu^{3+}$ or $Tb^{3+}$ complexes) to label antibodies. Aminopolycarboxylic acid chelates bind the metal ion strongly enough to keep it associated with antibody during the antigen-antibody reaction, but have minimal fluorescence. Rare earth fluorescence is developed by ligand exchange with a mixture of an aromatic diketone, which replaces the aminopolycarboxylic acid as chelator, a detergent to solubilize the highly insoluble diketone through micelle formation, and a Lewis base to make the fluorescence yield less sensitive to solvent quenching. In order for the extraction to take place in a reasonable time, acid pH must be used. The fluorescence of the resulting chelates is characterized by relatively long lifetimes compared with those of typical sources of fluorescent "noise", e.g., serum components. If a pulse of light is used to excite sample fluorescence, the "noise" fluorescence decays much more rapidly than the antibody-related fluorescence. This makes it possible to wait until "noise" fluorescence becomes minimal before detecting antibody-related fluorescence (hence the name time-resolved fluorescence), thereby improving the signal-to-noise ratio. However, measurement time is increased.

Reagents comprising non-biological particulate materials, e.g. glass, plastic or metallic microspheres, and a detectable reporter are routinely used, inter alia, in the measurement of blood flow. Blood flow may be measured by injecting the detectable microspheres into the bloodstream of a test subject, making an initial measurement of the microspheres present in a volume of the test subject's blood that was withdrawn at a known rate, recovering biological tissue of interest from the test subject, determining the number of microspheres present in a tissue sample of predetermined size and calculating the blood flow to the tissue of interest based on the number of microspheres determined to be present in the tissue sample. The reporters proposed for use heretofore in blood flow measurement have been radioisotopes, colored dyes or color-producing enzymes.

The use of radiolabelled reagents in bio-analytical procedures is of concern from the standpoint of possible radiation effects on personnel performing the measurement, safe disposal of the radioactive test subjects and cost of equipment, which includes a gamma counter to measure radioactivity, lead shielding to protect against radiation exposure and appropriate storage facilities for the radiolabelled materials.

Particulate reagents labelled with colored dyes have been proposed as a way of avoiding many of the concerns associated with use of radiolabelled reagents; however, the implementation of analytical procedures using such colored particle reagents have other serious drawbacks, particularly with regard to determining the number of the colored particles present in the tissue sample. Up to now, this determination has involved physically counting the colored particles, which have a dye permanently incorporated therein. Particle counting may be accomplished by manual or automated procedures, neither of which is entirely satisfactory. Manual counting of the colored particles, using a hemacytometer, is slow, tedious, labor intensive and susceptible to errors. Automated counting, on the other hand, requires sophisticated imaging equipment, which is also subject to errors and which entails considerable expense.

From the foregoing, it is apparent that a need exists for improved bio-analytical methods which can be performed at reduced cost, and yet enable accurate and reproducible determinations of a broader range of analytes, and more efficient measurements of biological conditions, as compared with the above-described prior art techniques.

SUMMARY OF THE INVENTION

In accordance with the present invention, there is provided a method for separating a compound comprising a bio-affecting substance, whether it be a diagnostic, therapeutic or prophylactic agent, from a carrier bearing such compound. The separation method of the invention may be used in conjunction with various bio-analytical techniques, including, without limitation, cell screening and blood flow measurement, so as to avoid the above noted deficiencies inherent in such techniques, as currently practiced.

In performing the method of the invention, any carrier capable of functioning as a vehicle for the bio-affecting compounds which are described hereinbelow, is contacted with an extractant which is immiscible with the carrier. Because the extractant and the carrier are immiscible, two distinct phases are produced which are referred to herein as the extractant phase and the carrier phase. The conditions under which the extractant and carrier are contacted are such that the molecular integrity of the bio-affecting compound is maintained and a major amount of the compound originally associated with the carrier is transferred to the extractant phase.

According to one embodiment, the separation method of the invention is used in separating from particulate, biological or non-biological carrier materials or from animal or plant tissue, compounds of the formula $R$—$B$—$R_1$, wherein B represents a bio-affecting substance and R and/or $R_1$ represent hydrocarbon substituents that impart binding affinity for the selected carrier. Consequently, covalent coupling of these compounds to the carrier material is not necessary in the method of the invention, as it is in numerous prior art bio-analytical techniques employing labelled analytes and/or reagents. Furthermore, because the compound comprising the bio-affecting substance is stably associated with its carrier, there is no appreciable leakage of the compound in the environments generally encountered during use and the compound is not transferred to other structures with which the carrier comes into contact. Nevertheless, compounds of the above formula may readily be dissociated from the carrier by retrieval with an appropriate extractant, preferably an organic protic solvent.

The separation method of the invention is particularly useful in bio-analytical techniques involving fluorometric determinations, as fluorescence efficiency is increased substantially by transfer of the fluorescent reporter from an aqueous to an organic phase, and concentration of the reporter prior to fluorescence measurement.

As applied to cell screening, the separation method of the invention may be used to provide information of the type obtainable from flow cytometry, concerning changes in cell number. Moreover, unlike flow cytometry, the extraction method of the invention can provide such information with respect to a wide range of tissue types.

As applied to blood flow measurement, the separation method of the invention provides a decidedly more efficient way of determining the number of fluorochrome-bearing microspheres in a tissue sample of interest by extracting the fluorochrome from the microspheres and correlating the measured intensity of the separated fluorochrome to the number of microspheres present in the tissue sample.

Extraction of the reporter substance, in either cell screening or blood flow measurement, provides an added benefit in that determination of the reporter can be achieved using relatively simple and inexpensive detection equipment and procedures, e.g. fluorometry.

Other advantages of the present invention will be apparent to those skilled in the art upon consideration of the accompanying drawing in conjunction with the detailed description of the invention presented below.

BRIEF DESCRIPTION OF THE DRAWINGS

Referring to the drawings herein.

DETAILED DESCRIPTION OF THE INVENTION

Figure 1A:
FIGS. 1A–1E are diagrammatic representations of phase separations, including optimal (FIG. 1E), suboptimal (FIGS. 1C and 1D) and impracticable (FIGS. 1A and 1B) systems, produced as a result of carrying out the separation method of the invention on tissue samples bearing an extractable fluorescent reporter.
Figure 1B:
Figure 1C:
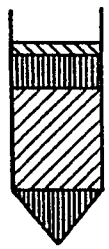
Figure 1D:
Figure 1E:

The term bio-affecting compound is used herein to refer to a wide variety of different compounds useful in the diagnostic, therapeutic, prophylactic or other treatment of humans or animals. The compounds useful in diagnostic applications of the invention include those which enable determination or detection of a physiological condition or state by an in vivo or in vitro test. The therapeutic compounds useful in therapeutic applications of the invention include those capable of preventing, alleviating, treating or curing abnormal or pathological conditions of the living body. The bio-affecting compounds useful in the practice of this invention further include those capable of maintaining, increasing, decreasing, limiting or destroying a physiologic body function, as well as substances for protecting a living body by inhibiting, killing, modifying or retaining a microorganism or antigen thereof.

The bio-affecting compounds used in the practice of this invention are represented by the formula R—B—$R_1$ wherein B represents a bio-affecting substance and R and $R_1$ represent substituents independently selected from the group of hydrogen, alkyl, alkenyl, alkynyl, alkaryl or aralkyl, the hydrocarbon chains of which are linear or branched, the substituents being unsubstituted or substituted with one or more non-polar functional groups, one of R or $R_1$ having at least two linear carbon atoms and the sum of the linear carbon atoms in R and $R_1$ totalling at least four.

A preferred class of bio-affecting compounds are those in which at least one of B, R or $R_1$ comprise a detectable reporter moiety, such compounds being particularly useful in diagnostic applications of the present invention. Such compounds may comprise detectable reporters selected from the group of fluorescent, phosphorescent, light absorbent, radioactive, radiopaque, electrochemical or paramagnetic moieties.

Particularly preferred as reporter moieties are fluorochromes, including, by way of example, cyanine dyes and their derivatives, including, e.g., oxacarbocyanine, indocarbocyanine, thiocarbocyanine, or acridine dyes and derivatives thereof. Other useful classes of fluorochromes are the styrlpyridine, anthraquinone, coumarin, xanthene, phenoxazine, phenothiazine, or diphenylhexatriene dyes and derivatives thereof.

The invention will be described hereinbelow with particular emphasis on the use of fluorescent compounds as detectable reporters in diagnostic applications, such as cell screening. It should be understood, however, that the invention has a substantially broader range of utilities.

The R and/or $R_1$ groups of the bio-affecting compound are selected so as to promote stable association between the compound and its carrier. The term "stable association" is used herein to signify that the affinity of the compound R—B—$R_1$ for the carrier is greater than for any surrounding medium in which the carrier may be dissolved or suspended.

The affinity of the below-described reporter molecules for biological carriers such as cells is sufficiently strong that the reporter molecules remain associated with the lipid component of the cell membrane even when exposed to conditions or agents having a tendency to cause leakage or loss of materials from membrane-containing microcapsules. See e.g., P. Machy et al., Proc. Nat. Acad. Sci., U.S.A., 79:4148 (1982); and Monroe, Amer. Biot. Lab, 5:10–19 (1987). Unlike previous cell labelling methods, see for example V. Ghazarossian et al., Clin. Chem. 1, 34:1720 (1988) and U.S. Pat. No. 4,748,129, the stable association between these reporter molecules and the lipid component of a cell or virus membrane, in accordance with the present invention, is lost only when subject to conditions or agents which disrupt or destroy the integrity of the membrane's lipid component, such as by contact with detergents or lipid solvents which dissolve or disperse the lipid component.

On a quantitative basis, the expression "stably associated with", as used herein with reference to the broad range of useful carriers, signifies that greater than 80% of the reporter initially linked to a carrier remains linked with the carrier throughout the course of the analysis (as detected by physical separation of carrier from disassociated reporter substance), which is generally on the order of twenty-four hours.

Reporter substances capable of stable association with the carriers used in the separation method of the invention may comprise substances that exhibit a generally hydrophobic character, or that may include a moiety having at least one hydrophobic portion or domain serving to anchor the reporter molecule to the carrier. In the latter instance, the hydrophobic portion of the reporter molecule should link the molecule to the carrier sufficiently to cause it to remain stably associated therewith, even in an agitated solution or disrupted cell or tissue suspension.

A particularly useful group of reporter substances is represented by the formula:

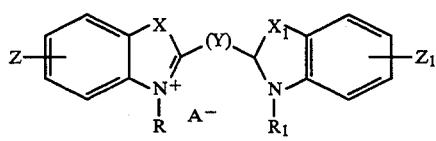
(I)

wherein R and $R_1$ are the same or different and represent substituents independently selected from the group of hydrogen, alkyl, alkenyl, alkynyl, alkaryl or aralkyl, the hydrocarbon chains of which having from 1 to 30 carbon atoms, and being linear or branched, said substituents being unsubstituted or substituted with one or more non-polar functional groups, one of R or $R_1$ having at least 12 linear carbon atoms, and the sum of the linear carbon atoms in R and R being at least 23;

X and $X_1$ may be the same or different and represent O, S, C(CH$_3$)$_2$ or Se;

Y represents a linking group selected from —CH=, —CH=CH—CH=, —CH=CH—CH=CH—CH=, or —CH=CH—CH=CH—CH=CH—CH=;

Z and $Z_1$ may be the same or different and represent substituents selected from the group H, alkyl, OH, NH$_2$, COOH, CONH$_2$, SO$_3$H, SO$_2$NH$_2$, NHNH$_2$, NCS, NCO, CONH-alkyl, CON-(alkyl)$_2$, NH-acyl, O-alkyl, NH-alkyl, or N(alkyl)$_2$, SH, S-alkyl, NO$_2$ or halogen, the alkyl groups comprising said Z substituents having from 1 to 3 carbon atoms; and A represents a biologically compatible anion.

A sub-group of useful reporter substances within the above-described group (I) includes compounds of the formula:

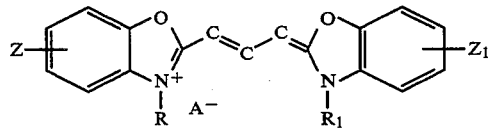
(II)

wherein
R and $R_1$ are the same or different and represent alkyl substituents, having from 1 to 30 carbon atoms, and being linear or branched, unsubstituted or substituted with halogen, one of R or R having at least 12 linear carbon atoms and the sum of the linear atoms in R and $R_1$ being at least 23;

Z and $Z_1$ may be the same or different and represent substituents selected from the group H, or lower alkyl having from 1 to 3 carbon atoms; and A represents a biologically compatible anion.

Of the compounds represented by formula II, particularly preferred reporter substances are 3-n-pentyl-3'-n-octadecyloxacarbocyanine iodide, 3-n-octyl-3'-n-octadecyloxacarbocyanine iodide, 3-n-propyl-3'-n-eicosanyloxacarbocyanine iodide, and 3-n-propyl-3'-n-docosanyloxacarbocyanine iodide.

Yet another subgroup of useful reporter substances within the above-described group (I) includes compounds of the formula:

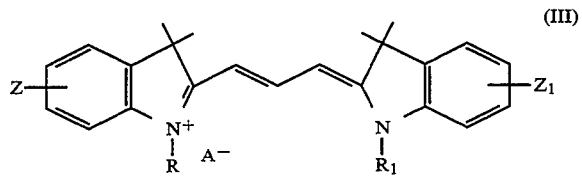
(III)

wherein
R and $R_1$ are the same or different and represent alkyl substituents, having from 1 to 30 carbon atoms, and being linear or branched, unsubstituted or substituted with halogen, one of R or $R_1$ having at least 12 linear carbon atoms and the sum of the linear atoms in R and $R_1$ being at least 23;

Z and $Z_1$ may be the same or different and represent substituents selected from the group H, or lower alkyl having from 1 to 3 carbon atoms; and A represents a biologically compatible anion.

Among the compounds represented by formula III, preferred reporter substances include: 1,1'-di-n-octadecyl-3,3,3',3'-tetramethylindolocarbocyanine perchlorate; 1-n-octadecyl-1'-n-pentyl-3,3,3',3'-tetramethylindolocarbocyanine perchlorate; 1n-docosanyl-1'-n-tetradecyl-3,3,3',3'-tetramethylindolocarbocyanine iodide; and 1-n-docosanyl-1'-n-propyl-3,3,3',3'-tetramethylindolocarbocyanine iodide.

A further group of useful reporter substances includes compounds of the formula:

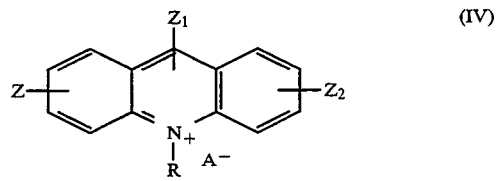
(IV)

wherein
R represents a substituent selected from the group of alkyl, alkenyl, alkynyl, alkaryl or aralkyl, the hydrocarbon chain of which is linear or branched, said substituent being unsubstituted or substituted with one or more non-polar functional groups, and having at least 23 linear carbon atoms;

Z, $Z_1$ and $Z_2$ may be the same or different and represent substituents selected from the group H, alkyl, OH, NH$_2$, COOH, CONH$_2$, SO$_3$H, SO$_2$NH$_2$, NHNH$_2$, NCS, NCO, CONH-alkyl, CON-(alkyl)$_2$, NH-acyl, O-alkyl, NH-alkyl, or N(alkyl)$_2$, SH, S-alkyl, NO$_2$, halogen, the alkyl groups comprising said Z substituents having from 1 to 3 carbon atoms; and A represents a biologically compatible anion.

Of the compounds represented by formula IV, a preferred reporter substance is 3,6-bis(dimethylamino)-10-n-hexacosanyl acridinium iodide. Other useful fluorochromes are 4-[4-didecylaminostyryl]-N-methylpyridinium iodide, N-3[3-Sulfopropyl]-4-[p- didecylaminostyryl] pyridinium inner salt and 2-[3-(1-n-docosanyl-benzoxazol-2-yliden)-1-propenyl]-6-iodo-1-n-tetradecyl-benzothiazolium iodide.

As used in the preceding description of the useful reporter substances, the term "non-polar functional group" refers to substituents such as O-alkyl, S-alkyl, halogen, N(alkyl)$_2$, Se-alkyl, NO, CN, CO-alkyl, C=N-alkyl, —SiMe$_3$, —O—SiMe$_3$ and the like.

Although fluorochromes are preferred as reporters in the separation method of the invention, the reporter may also comprise a substantially hydrophobic chelate-metal complex, preferably wherein the chelate-metal complex comprises a metal ion selected from the transition metal series whose atomic number is from 21–29, the lanthanide series whose atomic number is 59–66 and the actinide series whose atomic number is 91, said complex being detectable by nuclear magnetic resonance or luminescence. The chelate-metal complex may also comprise a paramagnetic metal ion selected from the group of Gd, Cr, Dy, Ni, Cu, Fe and Co.

The reporter may also comprise a substantially hydrophobic substance incorporating a detectable radioisotope. The radioisotope incorporated into the reporter substance is preferably selected from the group of radioactive carbon, hydrogen, nitrogen, phosphorus, fluorine, chlorine, iodine, sulphur, selenium, cobalt and chromium.

The foregoing classes of hydrophobic reporter substances are described in further detail, along with specific preparative procedures, in copending U.S. patent application Ser. No. 189,192, which is commonly assigned with the present application. The entire disclosure of Ser. No. 189,192 is incorporated by reference in this specification, as if set forth herein in full. The indocarbocyanine dyes are readily prepared following the general reaction scheme for oxacarbocyanine dyes set out in Ser. No. 189,192, substituting the appropriate indole derivatives for the benzoxazole derivatives used as starting materials in the reaction there described.

The reporter substances just described are characterized by having relatively long chain hydrocarbon substituents or "tails" that impart the requisite hydrophobicity/lipophilicity for stable association with particulate biological and non-biological carriers, as well as with tissue. Once these compounds become bound to a carrier, they do not easily dissociate. Consequently, the reporter does not leak from the carrier and thus is not liable to be transferred to another carrier, or to other biomolecules or cell-associated structures.

The carriers used in the separation method of the invention may comprise particulate biological materials, including, specifically, bio-membrane containing entities, such as cells and certain viruses. As used herein, the term "cells" refers to prokaryotic cells, e.g. bacteria, and eukaryotic cells, e.g. tumor cells, white blood cells, red blood cells and platelets, as well as any genetic manipulation or modification thereof using recombinant DNA techniques, or naturally-occurring mutations of either class of cells. The cells may be viable or non-viable, e.g. and red cell ghosts. In addition, plant or animal tissue, by which is meant any organized structure or aggregation of cells, which can be viable or non-viable, may serve as the carrier.

Suitable carriers may also take the form of particulate, non-biological materials which may be of inorganic or organic origin. Representative examples of such materials are glass, ceramic, metallic or polymeric particles, e.g. polystyrene, divinylbenzene, nylon, agarose, latex or the like. The carriers may be prepared from magnetic materials to facilitate separation of the carrier from tissue or solution containing the carrier, prior to extraction. Of course, combinations of these materials, e.g. protein or other bio-compatible polymer coated magnetic microspheres, may be used, if desired. Liposomes may also be used as carriers in the practice of this invention. Such particulate materials are produced as microspheres, the diameter of which are generally within the range of 0.1 to 100 microns. Preferably, the average particle size of the microspheres is on the order of about 15 microns in diameter. Microspheres of this size are commercially available from several sources, including Coulter Electronics, Hialeah, Fla. (polystyrene microspheres) and Polysciences, Inc., Warrington, Pa. (latex, polystyrene and magnetic microspheres).

The class of carriers which may be used in carrying out the method of the invention also encompasses various aqueous media, which may be any water-containing medium that is not miscible with the extractant, including, for example, water, tissue culture medium, phosphate-buffered saline or water-based fixative solutions. The several carriers described above may be used in various combinations, typical examples being cell suspensions or microsphere suspensions in phosphate buffered saline. The term "carrier phase", as used herein, refers to the carrier and any surrounding medium in which the carrier is, or may have been dissolved or suspended, which medium is substantially immiscible with the extractant.

Details regarding the coupling of the above-described reporter substances to biomembrane-containing entities are provided in U.S. Pat. No. 4,783,401 to Horan et al., the entire disclosure of which is incorporated in this specification by reference, as if set forth herein in full. In general, coupling of the reporter substance to cells involves suspension of the cells in a suitable medium, e.g., 300 mOs per liter sucrose, at a concentration of $10^5$ to $10^9$ ml., followed by addition of the reporter substance to the cell suspension in an amount of about 1–100 $\mu$M and incubation of the suspension for about 5 minutes, at about 20°–30° C. A similar procedure may be followed for coupling of such reporter substances to tissue provided the tissue is thoroughly washed prior to coupling.

In coupling the above-described reporter substances to particulate, non-biological materials, e.g. polystyrene microspheres, the carrier material is first washed, treated with a concentrated weak acid and washed using a buffer solution overlayered with a small amount of a reagent, such as ethanol, which reduces the surface tension and allows the microspheres to be pelletted. The acid pretreatment serves to strip the microspheres of any blocking agents used to prevent aggregation and impart an electrical charge to the microspheres which is believed to aid in coupling of the reporter substance thereto. After pretreating in this manner, the microspheres are then contacted with the reporter substance, which has a natural affinity for the microspheres due to its hydrophobic character. Excess reporter substance is thereafter removed by washing. The same general procedure may be used to couple reporter substances to other non-biological particulate carriers.

The reporter moiety may be more firmly coupled to the non-biological, particulate carriers by forming covalent bonds therebetween. For example, fluorochromes having the structure of formula (I), above, may be bound through the substituent Z or $Z_1$ to polymer coated microspheres through functional groups present in the polymer coating. Of course, the use of microspheres covalently coupled to a reporter in the practice of this invention would require chemical treatment to sever the covalent bonds prior to extraction of the reporter from the carrier.

The accuracy and reproducibility of quantitative test results using the separation method of the invention depend on substantially complete removal of the reporter substance from the carrier. This is especially true for the quantitative determination of low frequency events, such as microsphere enumeration from tissue, e.g. as in blood flow measurement, in which recovery of at least 75% of the reporter substance is required in practice. Substantially complete removal of the reporter substance from the carrier depends, in turn, on the nature of the extractant used in carrying out the separation method. The extractant should be substantially immiscible with the carrier phase (i.e. less than about 20% soluble in any liquid medium comprising the carrier phase), and should effect greater than 75% removal of the reporter substance from the carrier phase.

A number of solvents have been evaluated as possible extractants for use in the method of the invention. This evaluation involved extraction of the reporter 1-n-docosanyl-1'-n-tetradecyl-3,3,3',3'-tetramethylindocarbocyanine from water, as the carrier phase, and measurement of the fluorescent intensity of the reporter in the extractant phase. The results of this evaluation are set forth in Table I.

TABLE I

| Extractant | Extractant Phase | Carrier Phase | Total | % of Total in Extractant Phase | |
|---|---|---|---|---|---|
| HEXANE | 62.45 | 28.34 | 90.79 | 68.79 | |
| " | 65.41 | 27.90 | 93.31 | 70.10 | |
| " | 51.94 | 29.64 | 81.58 | 63.67 | 67.52 |
| CARBON TET | 15.39 | 7.30 | 22.69 | 67.82 | |
| CARBON TET | 16.25 | 6.17 | 22.42 | 72.48 | |
| CARBON TET | 17.51 | 6.48 | 23.99 | 73.00 | 71.10 |
| HEPTANE | 93.27 | 27.12 | 120.39 | 77.47 | |
| " | 95.44 | 27.12 | 122.56 | 77.87 | |
| " | 66.80 | 30.29 | 97.09 | 68.80 | 74.72 |
| TOLUENE | 15.65 | 23.08 | 38.73 | 40.41 | |
| " | 19.51 | 20.60 | 40.11 | 48.64 | |
| " | 19.86 | 23.99 | 43.85 | 45.29 | 44.78 |
| XYLENE | 18.56 | 25.42 | 43.98 | 42.20 | |
| " | 28.16 | 21.30 | 49.46 | 56.93 | |
| " | 24.60 | 24.25 | 48.85 | 50.36 | 49.83 |
| 1-BUT | 2390.00 | 2.17 | 2392.17 | 99.91 | |
| " | 2428.00 | 10.26 | 2438.26 | 99.58 | |
| " | 2502.00 | 6.39 | 2508.39 | 99.75 | 99.74 |
| 2-BUT | 2222.00 | 78.40 | 2300.40 | 96.59 | |
| " | 2142.00 | 24.73 | 2166.73 | 98.86 | |
| " | 2168.00 | 17.30 | 2185.30 | 99.21 | 98.22 |
| 2MIP | 2585.00 | 2.87 | 2587.87 | 99.89 | |
| " | 2633.00 | 3.56 | 2636.56 | 99.86 | |
| " | 2689.00 | 1.39 | 2690.39 | 99.95 | 99.90 |
| 3MIB | 2916.00 | 51.15 | 2967.15 | 98.28 | |
| " | 2792.00 | 103.70 | 2895.70 | 96.42 | |
| " | 3035.00 | 88.14 | 3123.14 | 97.18 | 97.29 |

1-BUT = 1-butanol
2-BUT = 2-butanol
2MIP = 2-methyl-1-propanol
3MIB = 3-methyl-1-butanol From the data presented in Table I, it can be seen that of the four organic, protic solvents tested, 1-butanol, 2-butanol, 2-methyl-1-propanol and 3-methyl-1-butanol, each removes substantially all of the reporter substance present in the carrier phase. A dramatic increase in measured fluorescence intensity was obtained from the extractions performed using the organic, protic solvents, as compared with the extractions performed using non-polar, aprotic solvents. Although other specific organic, protic solvents have not actually been evaluated, it is believed that any organic, protic solvent, such as m-cresol, would produce results similar to those obtained with the organic, protic solvents that were evaluated.

Using non-polar, aprotic organic solvents, namely hexane, carbon tetrachloride, heptane, toluene and xylene, only a portion of the total amount of reporter substance could be extracted. The use of organic, aprotic solvents would thus provide a suboptimal method for the retrieval of reporter substances. Such method would, nonetheless, have utility in performing qualitative determinations such as bio-affecting compound localization to specific sites.

The separation method of the invention is conveniently carried out by placing the carrier, bearing a bio-affecting compound of the type described above, in a suitable extraction vessel, e.g. a centrifuge or culture tube, and adding the extractant to the vessel. Generally, the ratio of extractant phase to carrier phase in the extraction vessel will be in the range of 1:1 to 1:10. The contents of the vessel are then mixed and normal partitioning is allowed to occur. The vessel may be centrifuged to hasten partitioning. A sample of the extractant phase is tested to determine the amount of reporter substance present therein, using an appropriate detection device, e.g. fluorescence spectrometer in the case of a fluorochrome-labeled carrier, or a gamma or beta counter in the case of a radiolabeled carrier.

The procedure for measuring blood flow using the separation method of this invention is performed in the following manner. Microspheres bearing a reporter of the type described hereinabove are injected into the blood stream of a test animal and an initial measurement is made of the microspheres present in a volume of the blood of the test animal that was withdrawn at a known rate. Biological tissue of interest is then secured from the test animal, and the reporter is extracted from the microspheres in a tissue sample of predetermined size. Thereafter, the intensity of the extracted reporter is measured which is correlated to the number of microspheres present in the tissue sample, and the blood flow to the tissue of interest is calculated based on the number of microspheres determined to be present in the tissue sample.

In performing the method of the invention on tissue, an additional preliminary treatment is utilized for dissociation and solubilization of the tissue. Preferably, the tissue sample to be extracted is mechanically dissociated using a glass or electric homogenizer or blender. Satisfactory results have been obtained using approximately 1 gram of tissue and 2 ml. of water. An equal volume (2 ml.) of a suitable detergent is then added to fully solubilize the dissociated tissue and the tissue sample is thoroughly homogenized. While room temperature incubation is possible for certain tissue types, it is possible to expedite the process by heating the detergent/tissue homogenate to at least 60° C. for 60 minutes in a water bath. Extraction of the reporter substance from the tissue then proceeds according to the general procedure described above.

Alternatively, tissue may be solubilized using a strong base, such as sodium hydroxide or potassium hydroxide (approximate concentration being 1M or greater) and heating the tissue in the base. If desired, the tissue may be kept in more concentrated base (5M or greater) at room temperature (22°-23° C.) for longer periods of time (up to 18 hours) to produce dissolution, without adding heat, and obtain almost complete recovery of the reporter substance.

The operating conditions under which the method of the invention is carried out must be appropriate for the carrier material sought to be extracted, so as to minimize any adverse effect on the molecular integrity of the reporter, e.g. degradation, rearrangement or other structural or conformational change, which might tend to impair its extractability or detectability. For example, when a tissue sample coupled with a cyanine dye is solubilized with a strong base, the fluorescence of the cyanine dye is quenched under such basic conditions. The adverse effect produced by the basic conditions may be overcome by neutralizing the tissue homogenate through the addition of concentrated acid, either before or after extraction. Addition of the neutralizing acid restores the fluorescence of the cyanine dye.

In the preferred tissue solubilizing procedure described above, it is important to use a detergent or other solubilizing agent capable of solubilizing the tissue without diminishing the immiscibility between the extractant phase and the carrier phase, or causing undesired accumulation of interfering substances at the interface between the extractant phase and carrier phase or transfer of tissue residue to the extractant phase. The desired separation will not be achieved if the detergent solution solubilizes the tissue while causing the extractant phase and the carrier phase to become miscible. Nor will the desired separation occur if the tissue resists solubilization and, after centrifugation, accumulates at the interface between the extractant and carrier phases, or is transferred into the extractant phase. The latter problem tends to minimize the volume of the extractant phase available for sampling and reduces the signal to noise ratio. For this reason also, when a strong acid or base is used as the tissue solubilizing agent, neutralization is preferably carried out after extraction and separation of the extractant phase from the carrier phase. Otherwise, addition of the neutralizing acid prior to extraction will cause tissue and proteins to accumulate at the interface between the extractant phase and the carrier phase, or to be transferred into the extractant phase, thereby interfering with the separation of the two phases.

Various cationic, anionic, zwitterionic and non-ionic detergents have been evaluated for use in the separation method of this invention, as applied to tissue samples. Detergents were evaluated according to the following procedure:

(i) Solutions (0.31M, or approximately 5-10% vol.-/vol.) of all the test detergents were prepared;

(ii) A series of liver homogenates were prepared, each in a polypropylene culture tube, using 1 gram of tissue and 2 ml. water;

(iii) A 2 ml. aliquot of the test detergent solution was added to each and mixed by vortexing;

(iv) A 10 μl quantity of one of the above described reporter substances ($1 \times 10^{-3}$M in ethanol) was added to each tube and thoroughly mixed by vortexing;

(v) The tubes were heated at 60° C. for one hour in a water bath;

(vi) n-butanol (1 ml.) was added as an extractant to each tube and the contents were mixed thoroughly by vortexing;

(vii) Each tube was centrifuged at 1,000×g for 10 minutes; and (viii) The extractant phase was tested to determine the amount of reporter substance present and compared with a control containing no tissue.

The contents of each tube were also examined for tissue sedimentation and extract separation. "Tissue sedimentation" refers to the solubilization (denaturation) of the tissue such that it becomes more hydrophilic and less hydrophobic. This is evidenced by the transition of the tissue from the extractant phase/carrier phase interface to the bottom of the tube. "Extractant separation" refers to the relative immiscibility of the extractant phase and the carrier phase.

The results of the detergent evaluations are set forth in Table II. The plus (+) and minus (−) signs indicate satisfactory and unsatisfactory results, respectively, for the tissue sedimentation and extractant separation examinations. The Critical Micelle Concentration (CMC) values given in Table II are those reported in the literature for the specific detergents evaluated. The CMC of a detergent is a measure of the detergent's tendency to form micelles spontaneously from amphiphiles, above a narrow concentration range. The CMC values given in Table II represent the millimolar concentration at which molecules of the detergent go from monomer configurations to aggregation or micellar formation in a temperature dependent fashion.

TABLE II

| | Tissue Sedimt. | Extractant separation | CMC |
|---|---|---|---|
| Anionic detergents | | | |
| Caprylic Acid | + | − | 351 |
| 1-Decanesulfonic Acid, Sodium Salt | + | − | 32.6 |
| Deoxycholic Acid, Sodium Salt | − | − | 5 |
| Glycodeoxycholic Acid, Sodium Salt | + | − | 2 |
| Taurocholic Acid, Sodium Salt | + | − | 10–15 |
| Triton X-200 | − | − | |
| Triton QS-30 | − | − | |
| Triton GR-5M | − | − | |
| Cationic detergents | | | |
| Cetylpyridinium Chloride | + | − | 0.9 |
| Dodecyltrimethylammonium Bromide | + | − | 14 |
| Hexadecyltrimethylammonium bromide | + | − | 0.026 |
| Tetradecyltrimethylammonium Br | + | − | 0.28 |
| Zwitterionic detergents | | | |
| CHAPS | + | − | 8 |
| Non-Ionic detergents | | | |
| n-Decyl B-D-glucopuranoside | −/+ | −/+ | 2.2 |
| n-heptyl B-D glucopyranoside | −/+ | −/+ | 70 |
| n-Octyl a-D-glucopyranoside | −/+ | −/+ | 10 |
| Nonidet P-40 | −/+ | + | 0.29 |
| Triton X-100 | + | + | 0.24 |
| Triton X-114 | + | + | 0.20 |
| Triton X-405 | + | + | 0.81 |
| Triton DF-16 | −/+ | + | − |
| Triton N-101 | + | + | .085 |
| Other detergents | | | |
| Triton X-35 | −/+ | −/+ | − |
| Triton CF-32 | −/+ | −/+ | − |

Diagrammatic representations of the results of the detergent evaluation are illustrated in the accompanying FIG. 1. Optimal separation, i.e. clearly distinct extractant and carrier phases, with tissue residue (vertical lines) deposited at the bottom of the separation vessel, is illustrated in FIG. 1E. The separation shown as FIGS. 1C and 1D are considered suboptimal since a portion of the tissue residue has accumulated at the interface between the extractant phase and the carrier phase (FIG. 1D), or has been transferred into the extractant phase (FIG. 1C). FIGS. 1A and 1B represent impracticable separation techniques due to undesired miscibility of the extractant and carrier phases (cross-hatching), and/or distribution of the tissue residue throughout the two phases.

From Table II, it can be seen that only the non-ionic detergents tested allowed for clear separation of the extractant phase and carrier phase. Thus, the use of non-ionic detergents enables concentration of the separated reporter into the relatively small volume of the extractant phase and minimizes extraneous noise from the tissue components. From the data in Table II it also appears that the detergents giving the best extraction results are the polyethoxylated linear alcohol and polyethoxylated substituted phenol non-ionic detergents (Nonidet P-40, Triton X-100, X-114 and X-405, DF-16 and N-101) having relatively low CMC values.

The ability to successfully extract bio-affecting compounds of the formula $R—B—R_1$ from any of the above described carriers is dependent upon the nature of the bio-affecting substance, B, and in particular the substituents R and $R_1$. In order to quantitate the influence of the substituents R and $R_1$ on extraction efficiency, tests were conducted using an oxacarbocyanine having R and $R_1$ substituents of varying lengths, between 4 and 36 linear carbon atoms. These tests were conducted according to the following procedure:

(i) Solutions of each of the reporter substances were prepared ($1 \times 10^{-3}$M in ethanol);

(ii) A 10 μl aliquot of each of the reporters was placed in a polypropylene culture tube together with 1.0 ml. water and thoroughly mixed by vortexing. Thereafter 1.0 ml. of butanol was added to each tube and thoroughly mixed by vortexing. Each tube was centrifuged at 2,000 rpm for 10 minutes to separate the extractant phase from the carrier phase. The amount of reporter in the extractant phase was then measured by transferring 10 μl of the extractant phase to 90 μl of ethanol and measuring the fluorescence in a fluorescent light reader. The amount of reporter in the carrier phase was measured in the same manner after aspirating the extractant phase;

(iii) A second set of polypropylene culture tubes was prepared, each containing 10 μl of one of the dyes listed in Table III, together with 0.5 ml. water and 0.5 ml. of the detergent PEG (9-10) p-t-octylphenol (Triton X-100). The relative amount of the reporter substance in the extractant and carrier phase of each tube was thereafter measured, in the manner described in the preceding paragraph;

(iv) The percentage of reporter extracted was calculated by dividing the signal from the extractant phase by the sum of the signals from the extractant and carrier phase for each reporter tested;

(v) The percentage of reporter extracted versus the sum of the linear carbons in substituents R and $R_1$, for the carrier phase comprising water alone and the detergent solution was plotted. The resulting graph is illustrated in FIG. 2.

Figure 2:
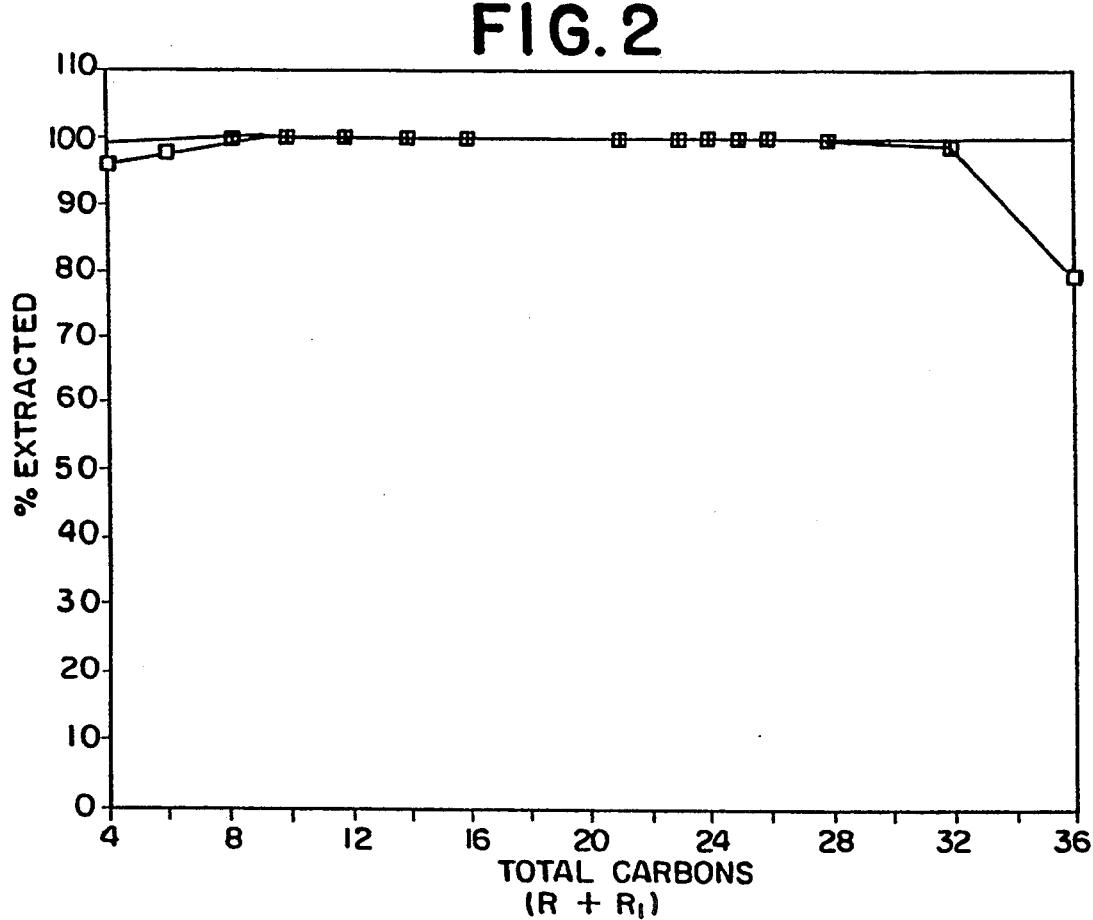
FIG. 2 is a graphic representation of the extraction efficiency, for separation from an aqueous carrier, of a series of fluorescent reporters, having the formula, R—B—$R_1$, wherein B is a fluorochrome and R and $R_1$ are aliphatic hydrocarbons of varying length, as a function of the combined length of the hydrocarbon substituents (R+$R_1$); the squares ( ) signify extraction from water alone, whereas the crosses (+) signify extraction from a detergent solution.

FIG. 2 shows that there was greater than 95% extraction of the total signal into the extractant phase under almost all conditions. This test establishes that the separation method of the invention may be successfully applied using all of the reporter substances tested in which the sum of the saturated carbon atoms in R and $R_1$ totaled 4 or more.

Several reporter compounds with different reporter moieties (B) were tested to evaluate the contribution of the reporter moiety to overall extraction efficiency. These tests were performed according to the five-step procedure described immediately above, except that 0.5 ml. butanol was used in step 2. The results of these tests are set forth in Table III.

TABLE III

| Reporter Moiety | R + $R_1$ | % Extraction into immiscible organic | |
|---|---|---|---|
| | | From water | From detergent |
| Acridine | 22 | 99.3% | 99.2% |
| Acridine | 18 | 99.5% | 99.3% |
| Acridine | 26 | 98.9% | 99.9% |
| Acridine | 24 | 99.6% | 96.5% |
| Thiacarbocyanine | 4 | 99.7% | 98.1% |
| Indocarbocyanine | 10 | 99.9% | 99.9% |
| Oxacarbocyanine | 4 | 96.2% | 99.2% |

From the data in Table III, it can be seen that all of the fluorescent reporter compounds tested were withdrawn into the organic solvent used for extraction.

The following examples provide further information regarding the manner and process of making and using the present invention and set forth the best mode contemplated by the inventors for carrying out the invention. The examples are provided for illustrative purposes only and are not to be construed as limiting the invention in any way.

EXAMPLE 1

Coupling of Reporter to Red Blood Cells

A citrate anticoagulant was prepared by dissolving sodium citrate (1.66 gm.) citric acid (0.206 gm.), sodium phosphate ($NaH_2PO_4$) (0.140 gm.) and glucose (1.61 gm.) in 63 ml. of distilled water and adjusting the solution to a pH of 5.6. The final solution was passed through a 0.22 micron filter for sterilization.

An iso-osmotic glucose solution was prepared by dissolving glucose (54.05 gm.) in one liter of distilled water. The osmolarity may be checked using a Fiske osmometer and adjusted to 320 mOsm if necessary.

A stock reporter solution of 1,1-ditetradecyl-3,3,3'3'-tetramethylindodicarbocyanine perchlorate ($2 \times 10^{-3}$M) was prepared by dissolving 1,628 ml. of the reporter compound in absolute ethanol. Sonication may be required to completely solubilize the compound.

Whole blood is collected aseptically using vacutainers containing sodium citrate or a syringe containing the prepared citrate anticoagulant in an amount equal to one tenth the total volume of the syringe. A small aliquot is reserved for flow cytometry or functionality testing. The blood is centrifuged at $100 \times g$ for ten minutes at room temperature to pellet red cells. The plasma containing platelets is removed and reserved, and the red cells are washed by adding iso-osmotic glucose in an amount equal to five times the volume of the packed red cell pellet. The cells should again be centrifuged at $100 \times g$ for ten minutes at room temperature and the supernatant aspirated. This wash which removes the plasma proteins and allows for more intense and uniform coupling of the reporter is repeated one more time. After the final centrifugation and aspiration of the supernatant, the red cells are resuspended in iso-osmotic glucose to a concentration of $4 \times 10^8$ cells/ml.

Prior to the addition of the reporter, the sample is pipetted or vortexed to insure that sedimentation has not occurred. Fifteen microliters of the stock reporter solution are added to each one milliliter of red cell suspension. The sample is immediately mixed to insure rapid and uniform distribution of the reporter in solution. After approximately five minutes a small aliquot is removed for microscopic observation. A ring is drawn on a glass microscope slide using a wax pencil and a small sample of the cells in the reporter solution is placed within the wax ring. A coverslip is placed on the slide and the sample is observed. The use of the wax ring lessens discocyte-echinocyte transformation due to the glass slide and coverslip. Use of plastic slides and coverslips will also prevent this transformation. In this way one can insure that the red cell structure is maintained throughout the coupling procedure while insuring that intense and uniform reporter coupling has occurred. Cells should be uniformly coupled with reporter after five minutes and exposure times of longer than ten minutes should not be necessary.

After it has been determined that the cells are uniformly coupled to reporter, an equal volume of phosphate buffered saline (PBS) is added to the resulting suspension. Cells are centrifuged at $400 \times g$ for ten minutes at room temperature, and the supernatant is removed. There will usually be traces of free reporter visibly present in the supernatants after centrifugation and therefore the washing procedure using PBS containing calcium and magnesium must be repeated until the supernatants are devoid of reporter as measured by spectrofluorometry.

The resultant cells coupled with reporter may be suspended in an appropriate solution and used as such for further experimentation.

EXAMPLE 2

Coupling of Reporter to Polystyrene Microspheres

A quantity of from 1-10 million 15 micron diameter polystyrene microspheres (Coulter Electronics, Hialeah, Fla.) were placed in a glass culture tube and centrifuged at $400 \times g$ for 5 minutes to form a pellet, after which the supernatant was removed.

The microspheres were washed twice using PBS, by resuspending the microspheres in PBS, centrifuging and removing supernatant after each wash.

The microspheres were resuspended in 2 milliliters of concentrated glacial acetic acid, sonicated for 15 seconds and incubated at room temperature for 30 minutes.

A quantity of 6 milliliters of ethanol was admixed with the microspheres/acid mixture.

The microspheres were centrifuged at $400 \times g$ for 5 minutes to remove the acid/ethanol.

The microspheres were washed twice using tris buffered saline (pH-7.0) by resuspending the beads in 6 mls. of the tris buffer and mixing. A small amount of ethanol (1 ml.) was slowly layered over the tris buffer to prevent the beads from floating. Care was taken to layer the ethanol on top of the tris buffer without mixing.

The microspheres were coupled to a fluorochrome known as PKH-26 (available from Zynaxis Cell Science, Inc.) by using a final concentration of 100 $\mu$M of the fluorochrome in the supplied diluent solution. This was accomplished by placing 200 microliters of 1 millimolar stock solution of the fluorochrome into a polystyrene centrifuge tube, heating the tube and aspirating the ethanol in the vapor phase to reduce the amount of ethanol present and to concentrate the fluorochrome approximately 3 fold. The ethanol should not be totally evaporated. The concentrated fluorochrome stock solution is diluted in supplied diluent to a volume of 2 milliliters. The resulting fluorochrome solution was slowly added directly to the microspheres and mixed to obtain a uniform suspension. The fluorochrome-bearing microspheres were incubated at room temperature for 1 hour or longer.

For use in blood flow measurement, PBS (5 mls.) containing species specific albumin is added to wash the microspheres. Species specific proteins would be rabbit albumin, if the beads are to be injected into a rabbit, or mouse albumin if the beads are to be injected into a mouse. The microspheres are then centrifuged at $400 \times g$ for 5 minutes.

Finally, the microspheres were washed twice using either PBS or specific protein containing PBS to remove unbound fluorochrome.

EXAMPLE 3

Enumeration of Cells in Tissues

The method of this invention may be used to determine the number of cells which have migrated to a particular organ after i.v. injection of the cells coupled to a suitable reporter. In making this determination cells are labeled with the reporter compound such that a uniformly labeled population is obtained. The cells are adjusted to a concentration of $1 \times 10^6$ cells/ml. and ten fold dilutions are prepared such that a final concentration of approximately 10 cells/ml. is obtained. Additionally, a concentration curve is prepared using the reporter compound in the extractant solvent to equate the fluorescence obtained from the cell samples to a total compound concentration in milligrams of compound/ml. of extractant. A sample curve might start at 1 mg compound/ml. of extractant solvent and decrease in concentration to about 0.01 ng/ml.

A linear regression is performed to derive an equation to determine amount of reporter compound from fluorescence obtained. The fluorescence obtained from various samples is measured and the equation is used to determine the amount of compound present in the samples (i.e. ng of compound/ml.). Dividing the amount of compound obtained from the various cell concentration samples by the number of cells extracted determines the amount of compound per cell at the time of labeling.

Determination of the distribution of the cells in the test animal post-injection can be made using this extraction technique. The animal is sacrificed and the organs of interest are removed and weighed. A small sample (0.5-1 gram) of the tissue is dissociated according to the described method and the above-described extraction is carried out. An aliquot of the extractant phase is sampled and the amount of the reporter compound present is determined by the appropriate measurement technique (e.g. fluorescence spectroscopy for compounds in which R is a fluorescent moiety). These samples are run with a standard compound concentration curve for comparison and the amount of total reporter present is determined. The total amount of reporter compound present in the organ is calculated by:

ng reporter compound in 1 gram sample $\times$ total organ weight (in grams)=total compound.

The number of cells migrating to an organ can be calculated by:

$$\frac{\text{total reporter compound in organ}}{\text{dye/cell (measured at injection)}} =$$

number of labeled cells in organ post injection.

While various aspects of the present invention have been described and exemplified above in terms of certain preferred embodiments, various other embodiments will be apparent to those skilled in the art. For example, the method of the invention may be used in connection with therapeutic agent localization determinations. The invention is, therefore, not limited to the embodiments specifically described and exemplified above, but is capable of variation and modification without departing from the spirit of the invention, the full scope of which is delineated by the appended claims.

What is claimed is:

1. A method for measuring blood flow comprising
   (i) injecting into the blood stream of a test animal microspheres coupled to a bio-affecting compound having the formula R—B—$R_1$, wherein B represents a bio-affecting moiety and R and $R_1$ represent substituents independently selected from the group consisting of hydrogen, alkyl, alkenyl, alkynyl, alkaryl, and aralkyl, the hydrocarbon chains of said substituents being independently selected from the group consisting of linear, unsubstituted hydrocarbon chains, linear hydrocarbon chains substituted with at least one non-polar functional group, branched, unsubstituted hydrocarbon chains and branched hydrocarbon chains substituted with at least one non-polar functional group, and one of R and $R_1$ having at least two linear carbon atoms, the sum of the linear carbon atoms in R and $R_1$ totalling at least 4, and at least one of B, R and $R_1$ comprising a detectable reporter moiety;
   (ii) making an initial measurement of the microspheres present in a volume of the blood of said test animal that was withdrawn at a known rate;
   (iii) recovering biological tissue of interest from the test animal;
   (iv) extracting said bio-affecting compound from said microspheres in a tissue sample of predetermined size;
   (v) measuring the intensity of said reporter moiety of the extracted bio-affecting compound;
   (vi) correlating said measured intensity to the number of microsphres present in said tissue sample; and
   (vii) calculating the blood flow to the tissue of interest based on the number of microspheres determined to be present in the tissue sample.

2. A method according to claim 1, wherein said reporter moiety is selected from the group consisting of a fluorescent, phosphorescent, light absorbent, radioactive, radiopaque, electrochemical and paramagnetic moiety.

3. A method according to claim 1, wherein said reporter moiety is a fluorescent moiety selected from the group consisting of an oxacarbocyanine, indolocarbocyanine, thiacarbocyanine and acridine dye.

4. A method according to claim 1, wherein said bio-affecting compound is extracted from said microspheres with an organic protic solvent.

5. A method for measuring blood flow in tissue of interest of a test animal comprising:
   (i) providing a labelled carrier in the form of microspheres to which are coupled a bio-affecting compound having the formula R—B—$R_1$, wherein B represents a bio-affecting moiety and R and $R_1$ represent substituents independently selected from the group consisting of hydrogen, alkyl, alkenyl, alkynyl, alkaryl, and aralkyl, the hydrocarbon chains of said substituents being independently selected from the group consisting of linear, unsubstituted hydrocarbon chains, linear hydrocarbon chains substituted with at least one non-polar functional group, branched, unsubstituted hydrocarbon chains and branched hydrocarbon chains substituted with at least one non-polar functional group and one of R and $R_1$ having at least two linear carbon atoms, the sum of the linear carbon atoms in R and $R_1$ totalling at least 4, and at least one of B, R and $R_1$ comprising a detectable reporter moiety;
   (ii) injecting said labelled carrier into the blood stream of said test animal;
   (iii) making an initial measurement of said labelled carrier present in a volume of the blood of said test animal that was withdrawn at a known rate;
   (iv) recovering said tissue from said test animal;
   (v) extracting said bio-affecting compound from said labelled carrier in a sample of said tissue of predetermined size, thereby yielding a carrier phase and an extractant phase, said phases being mutually immiscible, a substantial portion of said bio-affecting substance being present in said extractant phase;
   (vi) measuring the intensity of said reporter moiety in said extractant phase;
   (vii) correlating said measured intensity to the number of microspheres present in said tissue sample; and
   (viii) calculating the blood flow to said tissue of interest based on the number of microspheres determined to be present in said tissue sample.

6. A method as claimed in claim 5, wherein B comprises said detectable reporter moiety.

7. A method as claimed in claim 6, wherein said detectable reporter moiety is a fluorochrome.

* * * * *